(12) United States Patent
Salvermoser et al.

(10) Patent No.: US 11,419,595 B2
(45) Date of Patent: Aug. 23, 2022

(54) INTERSPINOUS, INTERLAMINAR SPACE EXPANDER AND MEASUREMENT INSTRUMENT

(71) Applicant: Paradigm Spine, LLC, New York, NY (US)

(72) Inventors: Markus Salvermoser, Tuttlingen-Möhringen (DE); Stephan Eckhof, Rietheim-Weilheim (DE)

(73) Assignee: PARADIGM SPINE, LLC, New York, NY (US)

( * ) Notice: Subject to any disclaimer, the term of this patent is extended or adjusted under 35 U.S.C. 154(b) by 619 days.

(21) Appl. No.: 15/983,326

(22) Filed: May 18, 2018

(65) Prior Publication Data
US 2018/0333174 A1 Nov. 22, 2018

Related U.S. Application Data

(60) Provisional application No. 62/508,512, filed on May 19, 2017.

(51) Int. Cl.
| | |
|---|---|
| *A61B 17/02* | (2006.01) |
| *A61B 5/107* | (2006.01) |
| *A61B 5/00* | (2006.01) |
| A61B 17/70 | (2006.01) |
| A61B 90/00 | (2016.01) |
| A61B 17/16 | (2006.01) |
| A61B 5/22 | (2006.01) |

(52) U.S. Cl.
CPC ............ *A61B 17/025* (2013.01); *A61B 5/107* (2013.01); *A61B 5/4566* (2013.01); *A61B 5/224* (2013.01); *A61B 17/1671* (2013.01); *A61B 17/7065* (2013.01); *A61B 17/7067* (2013.01); *A61B 2017/0256* (2013.01); *A61B 2090/061* (2016.02); *A61B 2090/064* (2016.02); *A61B 2505/05* (2013.01)

(58) Field of Classification Search
CPC ..... A61B 5/4566; A61B 5/107; A61B 5/1671; A61B 5/7065; A61B 5/7067; A61B 2017/0256; A61B 2090/061; A61B 2090/064

See application file for complete search history.

(56) References Cited

U.S. PATENT DOCUMENTS

| | | | |
|---|---|---|---|
| 6,739,068 B1* | 5/2004 | Rinner ................. | A61B 17/025 33/783 |
| 2002/0072752 A1* | 6/2002 | Zucherman ........ | A61B 17/7074 606/99 |
| 2004/0059261 A1* | 3/2004 | Grinberg ................ | A61B 90/06 600/587 |
| 2004/0133132 A1* | 7/2004 | Chappuis ............. | A61B 5/1076 600/594 |
| 2004/0236342 A1* | 11/2004 | Ferree ................... | A61F 2/4684 606/102 |

(Continued)

*Primary Examiner* — Daniel L Cerioni
*Assistant Examiner* — Raymond P Dulman
(74) *Attorney, Agent, or Firm* — Farber LLC (57) ABSTRACT

An interspinous, interlaminar space expander and measurement instrument for preparing an interspinous, interlaminar space between adjacent vertebrae to receive an implantable interspinous, interlaminar stabilization device is provided. The instrument includes an indicator which measures both height of the space and applied force to maintain that height.

20 Claims, 7 Drawing Sheets

(56) References Cited

U.S. PATENT DOCUMENTS

| | | | | |
|---|---|---|---|---|
| 2004/0267279 | A1* | 12/2004 | Casutt | A61B 90/06 |
| | | | | 606/104 |
| 2006/0052795 | A1* | 3/2006 | White | A61B 90/06 |
| | | | | 606/102 |
| 2010/0114179 | A1* | 5/2010 | Moore | A61B 17/7032 |
| | | | | 606/308 |
| 2011/0029079 | A1* | 2/2011 | Paulos | A61F 2/0805 |
| | | | | 623/13.13 |
| 2012/0215262 | A1* | 8/2012 | Culbert | A61B 17/1606 |
| | | | | 606/279 |
| 2015/0320456 | A1* | 11/2015 | Field | A61B 17/7068 |
| | | | | 606/249 |

* cited by examiner

FIG. 5 ized interspinous, interlaminar stabilization devices are disclosed in U.S. Pat. No. 5,645,599 and U.S. Patent Application Publication No. 2017/0027619. Exemplary interspinous, interlaminar vertebral stabilization systems that can be securely attached to the spinous processes or lamina while being seated interlaminarly are disclosed in U.S. Pat. Nos. 7,922,750 and 9,370,382. These vertebral stabilization systems utilize bone fasteners or screws to secure the systems to bone.

For interspinous, interlaminar stabilization devices such as the types mentioned above, the proper size, fit and placement of the device is essential to the success of the clinical results. It is therefore desirable to provide an instrument that can assist in the proper sizing of the space to receive the implantable device so that the correctly sized implantable device is selected. Further, it is desirable to provide an instrument that can assist in expanding the interspinous, interlaminar space to properly receive the implantable device.

INTERSPINOUS, INTERLAMINAR SPACE EXPANDER AND MEASUREMENT INSTRUMENT

CROSS-REFERENCE TO RELATED APPLICATIONS

This application claims benefit of U.S. Provisional No. 62/508,512, filed May 19, 2017, the entirety of which is herein incorporated by reference.

FIELD

The present disclosure relates to surgical instruments, and more particularly to an interspinous, interlaminar space expander and measurement instrument for evaluating and preparing an interspinous, interlaminar space between adjacent vertebrae to receive an implantable interspinous, interlaminar stabilization device.

BACKGROUND

Disorders of the spine cause significant morbidity. These disorders include abnormalities of the vertebrae, the intervertebral discs, the facet joints, and connective tissue around the spine. These abnormalities can be due to a number of causes, including weakening of the bone from the natural aging process, mechanical injury or trauma, or degenerative disc disease. Such abnormalities can cause instability to the spine, allowing the vertebral column to become misaligned and consequently allow micromotion between adjacent vertebrae. Vertebral misalignment and micromotion may result in wear to the vertebral bony surfaces and ultimately cause severe pain. Further, these conditions are often chronic and progressive problems.

The treatments for spinal disorders can include long-term medical management or surgery. Medical management is generally directed at controlling the symptoms, such as pain, rather than correcting the underlying problem. For some patients, this may require chronic use of pain medications, which may alter patient mental state or cause other negative side effects.

Recently, a variety of interspinous, interlaminar stabilization devices have become available. These devices may be implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering spinal anatomy.

Currently available interspinous, interlaminar stabilization devices can be inserted and secured between adjacent spinous processes using a number of different mechanisms. For example, such devices can include sharp barbs or other surface projections that engage the bony surface of a spinous process. In addition, flexible ligaments or sutures can be placed around the implants and adjacent bone. However, it may be desirable to provide a more rigid and secure attachment to the spinous processes. For example, a rigid attachment may be desirable to prevent the interspinous, interlaminar device from migrating or slipping out of position. In addition, a rigid attachment may be desirable to limit movement and promote fusion at a selected vertebral level. Bone screws may be used to affix the devices to the spinous processes or to the laminar surfaces of the vertebrae.

SUMMARY

The present disclosure provides an interspinous, interlaminar space expander and measurement instrument for evaluating and preparing an interspinous, interlaminar space between adjacent vertebrae to receive an implantable interspinous, interlaminar stabilization device. The instrument includes an indicator which measures both the height of the space and the applied force necessary to maintain that height.

According to one aspect, an instrument for evaluating an interspinous, interlaminar space between adjacent vertebrae is provided. The instrument may comprise a pair of handles connected at a pivoting hinge, each handle having a gripping portion at one end and extending into a leg extension at another, each of the leg extensions terminating at a tip having a bearing surface for engaging a bone surface. In some embodiments, the leg extensions may extend at an angle relative to the handles. In some embodiments, the tips of the leg extensions may extend at an angle relative to the leg extensions. A spring bias mechanism may be provided between the pair of handles, and a combination distance and force measurement component may also be provided between the pair of handles.

The combination distance and force measurement component may be slidingly attached to one of the handles and fixedly attached to the other of the handles. A knob may be provided on a shaft extending from a main body of the component to keep the handles in relative fixed position. Movement of the gripping portion of the handles towards one another effects spreading apart of the tips. The units of distance may be mm, and the distance measured may represent the height of the interspinous, interlaminar space between the adjacent vertebrae. The units of force may be Newtons, and the force measured may represent the applied force to maintain the distance of the interspinous, interlaminar space between the adjacent vertebrae.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 2A-2D illustrate detailed views of the surgical instrument of FIG. 1, in which:

DESCRIPTION OF THE EMBODIMENTS

The present disclosure provides a surgical instrument configured to spread the laminar space between adjacent spinous processes to allow the insertion of an interspinous, interlaminar stabilization device therein. The instrument includes a combination size and tension indicator, to allow the user the ability to measure the height of the space as well as the stiffness or applied force required to keep that space open to that height.

Figure 1:
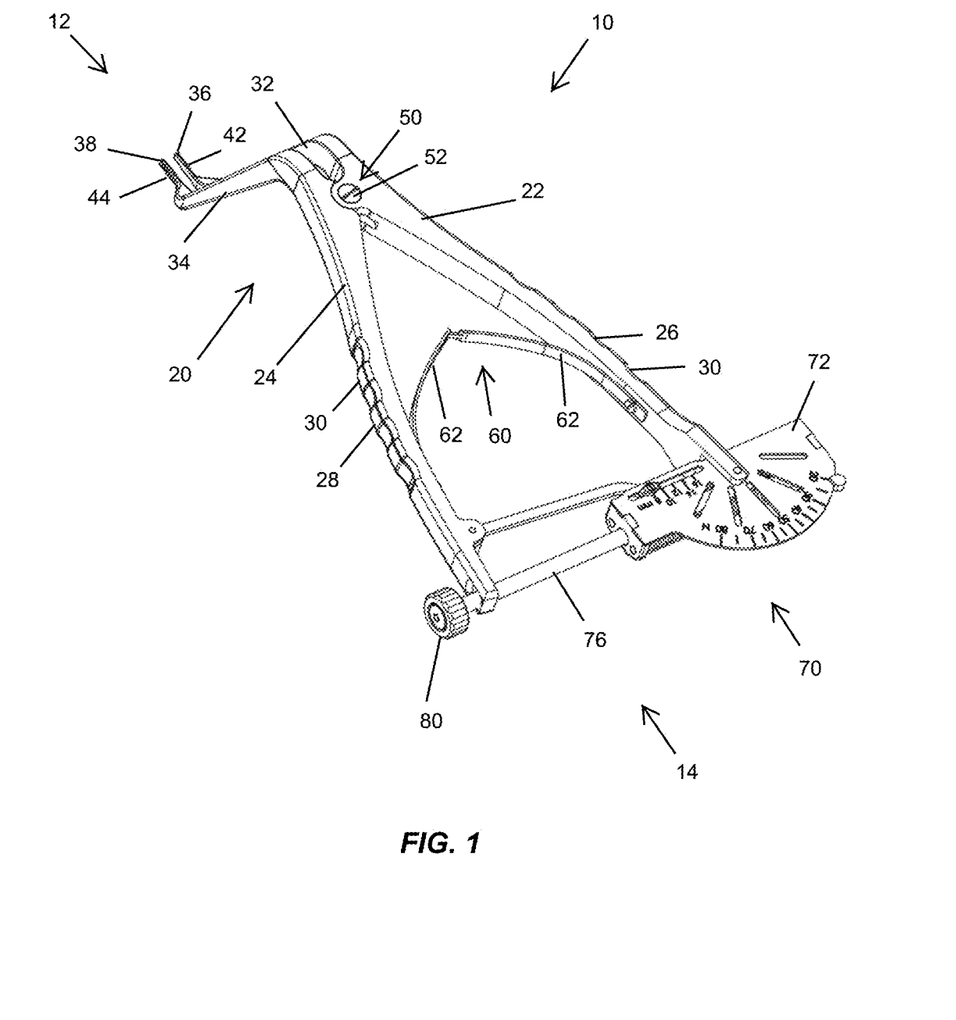
FIG. 1 illustrates a perspective view of an exemplary embodiment of a surgical instrument of the present disclosure.

Turning now to FIG. 1, a surgical instrument 10 for evaluating an interspinous, interlaminar space in accordance with the present disclosure is shown. The instrument 10 may include a main body 20 comprising a pair of elongate handles 22, 24, each handle 22, 24 extending into a bent leg extension 32, 34. The leg extensions 32, 34 may be angled at approximately a right angle or 90 degrees with respect to the handles 22, 24. Of course, it is understood that in some embodiments, the leg extensions 32, 34 may be provided without an angle (i.e., straight) or at a different angle relative to the handles 22, 24, such as an angle in the range of about 60 degrees to about 120 degrees, or in the range of about 75 degrees to about 105 degrees. Each of the leg extensions 32, 34, may terminate into a bearing surface 42, 44 located at the tips 36, 38 of the extensions. The tips 36, 38 may also be bent relative to the leg extensions 32, 34 at about 90 degrees, as shown in FIG. 1, or at an angle in the range of about 60 degrees to about 120 degrees, or in the range of about 75 degrees to about 105 degrees. The tips 36, 38 collectively serve as the working end 12 of the instrument 10, with the bearing surfaces 42, 44 being configured with a surface feature that enhances its grip on bone. For example, the surface feature may comprise teeth, protrusions, etchings, or surface roughenings.

The handles 22, 24 may be pivotally connected to one another at a hinged connection 50 that allows for a scissors, or see-saw, type movement of the handles 22, 24. In one embodiment, the hinged connection 50 may comprise a connector pin or screw 52 connecting the two handles 22, 24 together. Between the two handles 22, 24 a spring bias mechanism 60 can be provided for controlled movement of the handles 22, 24. As shown, the spring bias mechanism 60 may comprise a pair of interconnected leaf springs 62. Each of the handles 22, 24 may include a gripping surface 26, 28 that may comprise, as shown, a series of one or more grooves or indents 30 for better handling. Of course, it is understood that in other embodiments, other surface features may be provided instead of, or in addition to, the grooves or indents 30, such as for example, teeth, protrusions, coatings, etchings or surface roughenings.

A combination height and tension measurement indicator 70 connects the handles 22, 24 together at the operating or control end 14 of the instrument 10. The indicator 70 may be fixedly connected to a first handle 22, while being slidingly connected to the second handle 24. The indicator 70 may include a main body 72 having a channel 74 for receiving an elongate shaft 76, as shown in FIG. 2D. This shaft 76 may be configured to slidingly move up and down within the channel 74 of the main body 72. In one embodiment, the shaft 76 may be threaded at a portion along its length, in order to cooperate with a knurled nut or knob 80. This knob 80 can help maintain the position of the handles 22, 24 relative to one another, as will be described in greater detail below.

As shown in FIGS. 2A-2D, the main body 72 may be configured to provide two types of indicators and is able to measure two types of values: a size indicator for measuring the spreading distance, and a force indicator for measuring applied force. As shown in more detail in FIG. 2B, the main body 72 may include at one portion A a series of indicia or markings 84 representing units of tension or applied force between the handles 22, 24. The units of force markings 84 may represent Newtons (N), for instance. A pointer 86 may cooperate with the shaft 76 in order to indicate on the main body 72 which of the force markings 84 is selected, to indicate the amount of applied force.

Figures 2A, 2B, 2C:
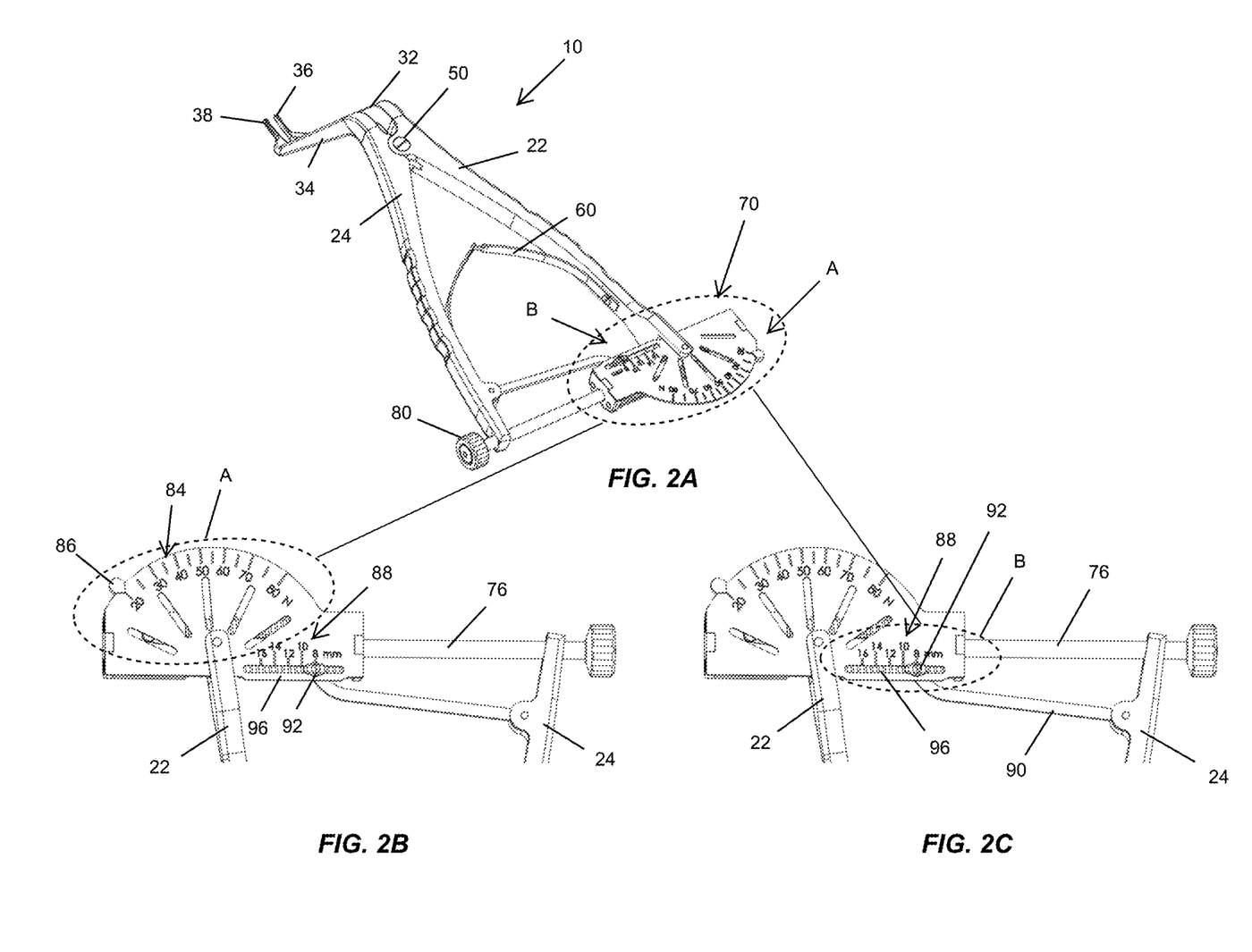
FIG. 2A illustrates another perspective view of the surgical instrument of FIG. 1.
FIG. 2B illustrates an enlarged view of the combination height and tension measurement indicator of the surgical instrument of FIG. 1 showing the force markings.
FIG. 2C illustrates an enlarged view of the combination height and tension measurement indicator of the surgical instrument of FIG. 1 showing the size markings.
Figure 2D:
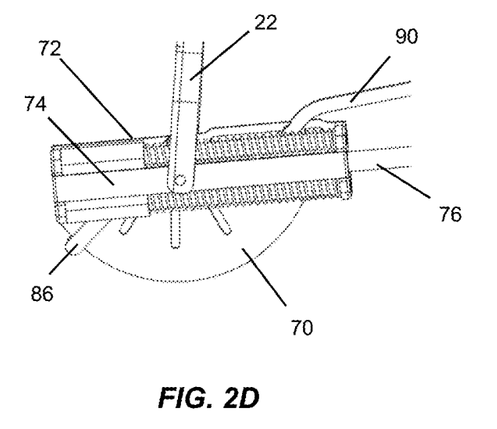
FIG. 2D illustrates a rear view of the combination size and force measurement indicator of the surgical instrument of FIG. 2A.

As shown in greater detail in FIG. 2C, the main body 72 may include along another portion B of its length a series of indicia or markings 88 indicating size measurements, such as in millimeter (mm) units, for instance. These size measurements represent spreading distance between the tips 36, 38, which also correspond to the height (or width depending on reference point) of the interspinous space 6. A pointer arm 90 extending from the second handle 24 and having a reference band 92 may be provided. The pointer arm 90 may be resting on the barrel 76, and be configured to move incrementally as the spreading of the handles 22, 24 occurs, as shown in FIG. 2D. Near the size markings 88 is a locator window 96 on the main body 72. This locator window 96 allows the user to read the size measurement based on where the reference band 92 is seen, as shown in FIG. 2C. As an example, a suitable range of markings 88 may comprise values of 8, 10, 12, 14, and 16 mm.

According to one exemplary method of using the surgical instrument 10, a user would place the bearings surface 42, 44 of the tips 36, 38 of the instrument 10 against the laminar surface of a pair of adjacent spinous processes. Similar to a normal laminar spreader, the user may squeeze the handles 22, 24 and spread the interspinous, interlaminar space to the desired height. The height or size may be determined by reading the indicated values on the combination measurement indicator 70. As the handles 22, 24 are held in the desired position to achieve the desired height/size of the space, the knob 80 can be turned and moved down the shaft 76 until the second handle 24 is held in its position under tension. At that point, the user can release his grip of the handles 22, 24 which will allow the instrument 10 to open up a small amount. The user can readjust the instrument 10 to the original position by tightening or turning the knob 80 once again against the second handle 24. The amount of force being applied can be read on the indicator 70, as previously described.

Figure 3A:
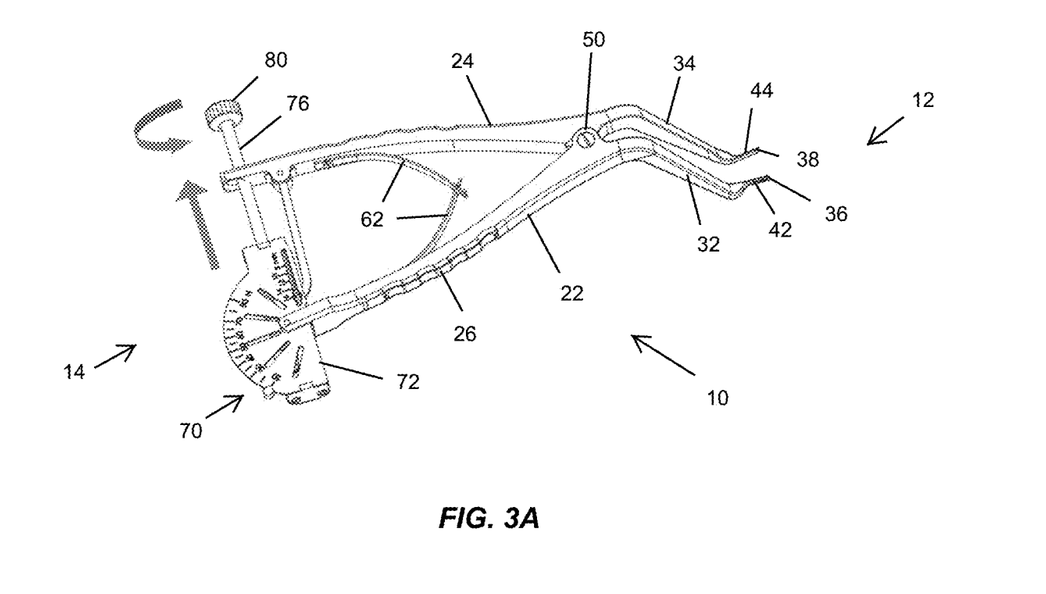
FIGS. 3A-3C illustrate an exemplary method of using the surgical instrument of FIG. 1 to measure spreading distance.
Figure 3B:
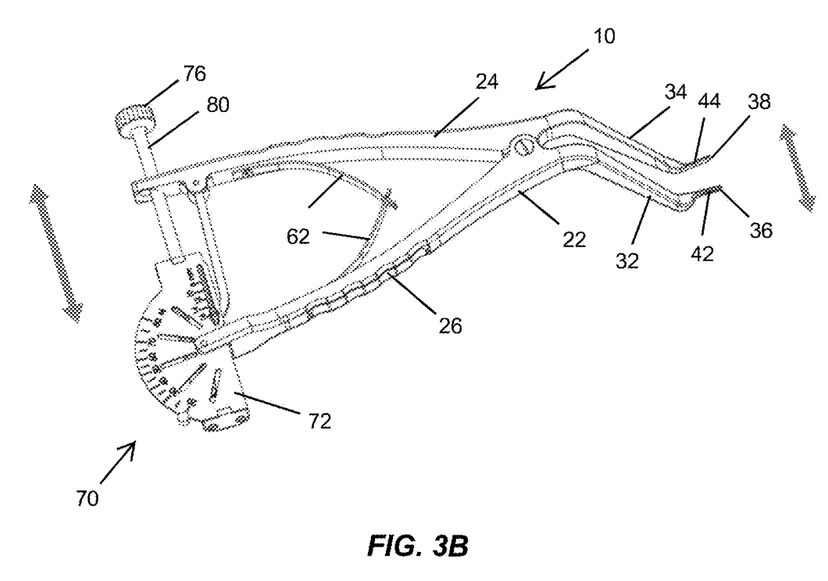
Figure 3C:
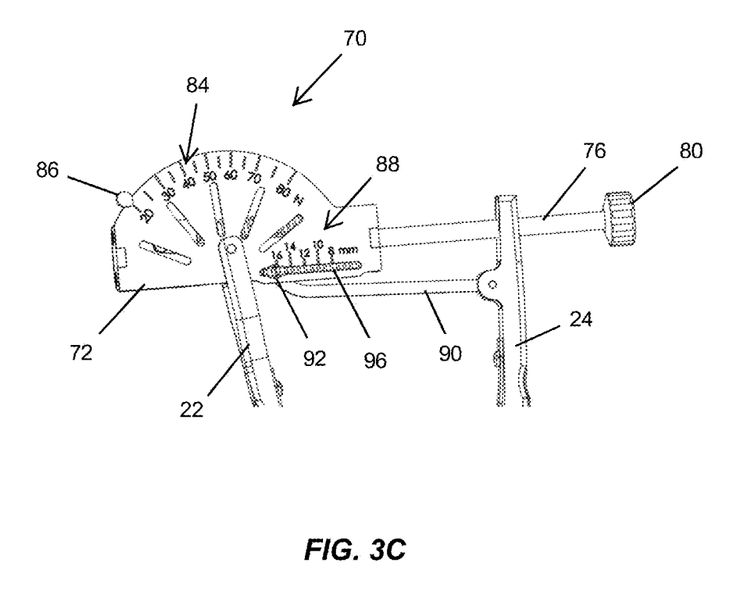

FIGS. 3A to 3C illustrate an exemplary method of using the instrument 10 to measure the spreading distance, or height (or width, depending on reference point) of the interspinous, interlaminar space 6. Prior to implanting an interspinous, interlaminar stabilization device 100 between two adjacent vertebrae 2, 4, the user may utilize this surgical instrument 10 to spread apart the space 6 that is intended to receive the device 100, and measure the space to ascertain the correct size trial or implantable device 100 for that patient. To do so, the instrument 10 may be inserted at its working end 12 between the vertebrae 2, 4 to be spread apart, as further described above. The knob 80 may be turned up to the end of the shaft 76 as shown by the arrows in FIG. 3A, allow the maximum degree of movement of the handles 22, 24. Squeezing the handles 22, 24 at their gripping portions 26, 28 moves the handles and the tips 36, 38 in the direction of the arrows shown, thereby spreading apart and/or measuring the height or distance between the interspinous space, as shown in FIG. 3B. The user can easily ascertain this measurement by viewing the band 92 of the pointer arm 90 through the window 96 to represent the size markings 88 on the main body 72 of the indicator 70, as shown in FIG. 3C. The size indication corresponds to the trial/implantable device size. For example, a measurement of 8 mm means that an 8 mm sized trial or implantable device should be used.

Figure 4A:
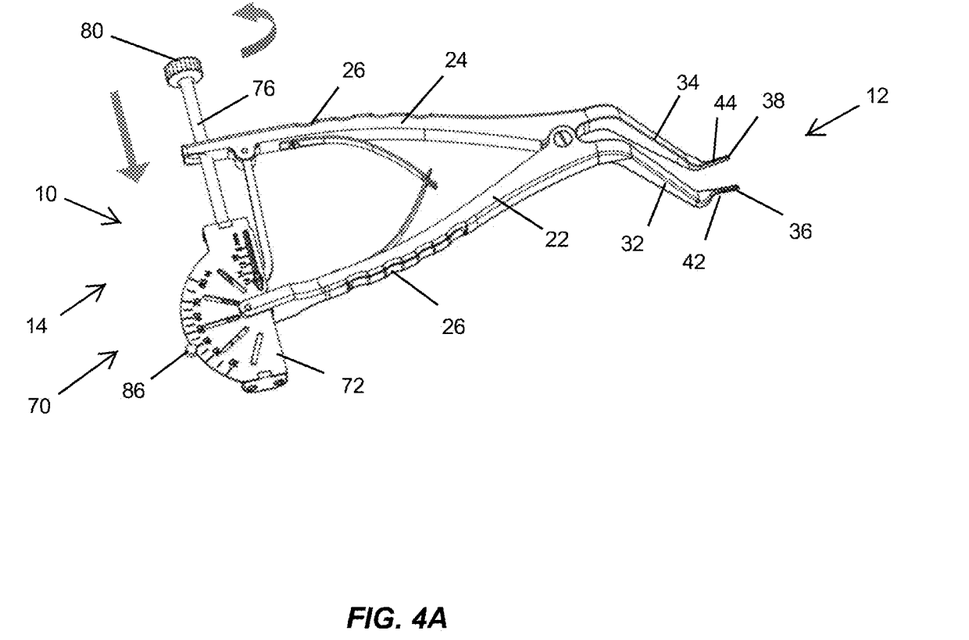
FIGS. 4A-4C illustrate an exemplary method of using the surgical instrument of FIG. 1 to measure applied force.
Figure 4B:
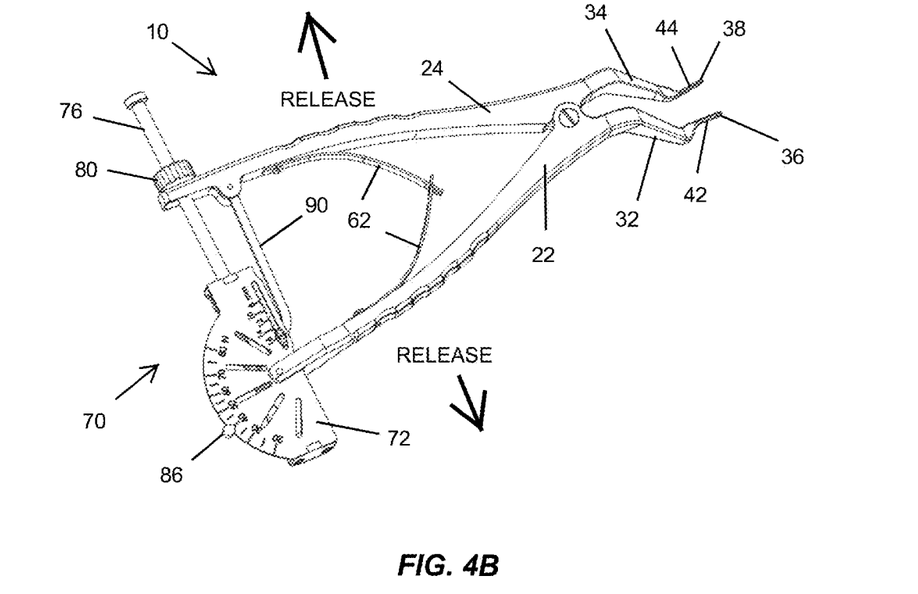
Figure 4C:
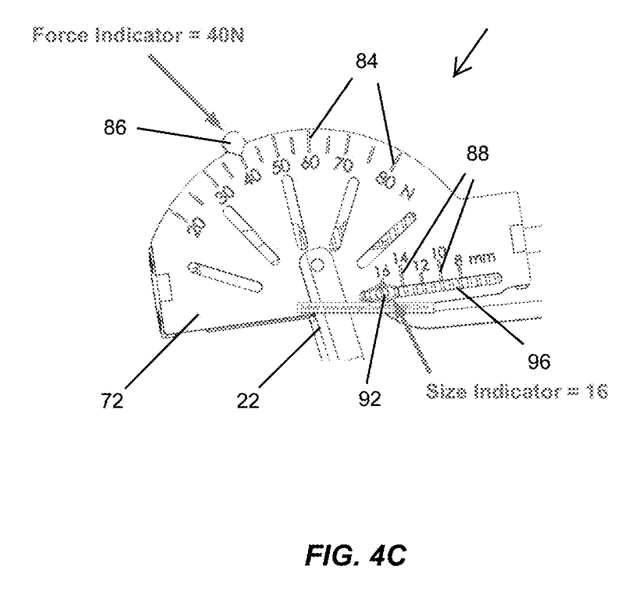
Figure 5:
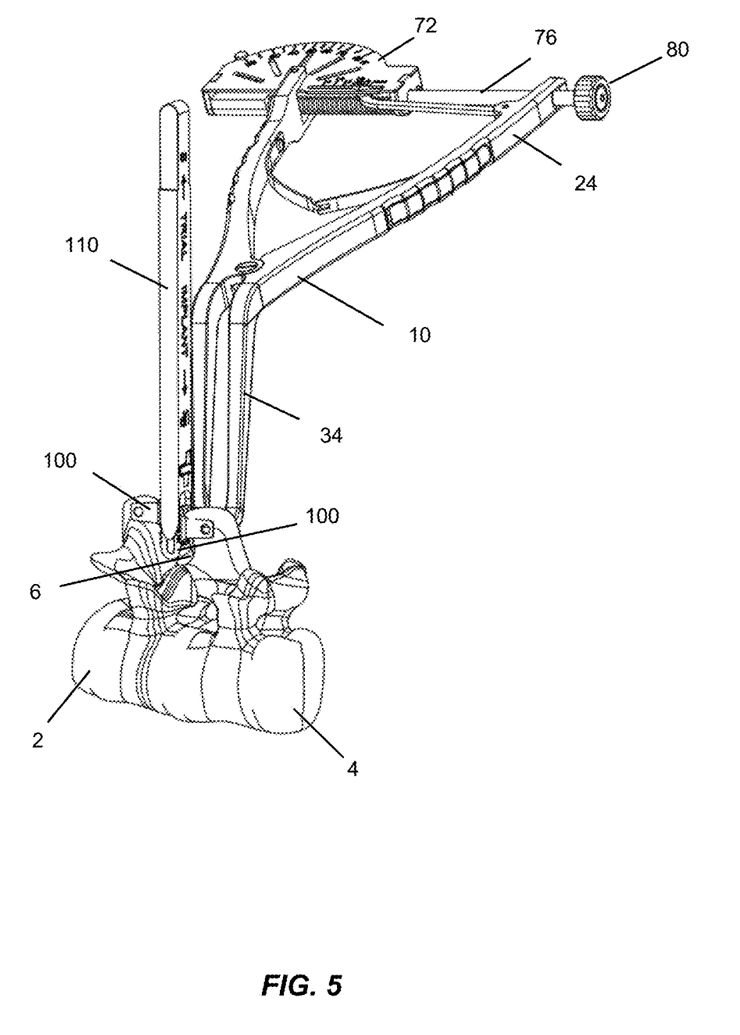
FIG. 5 illustrates the surgical instrument of FIG. 1 in use during trialing and implantation of an interspinous, interlaminar device.

FIGS. 4A to 4C illustrate an exemplary method of using the instrument 10 to measure the applied force in relation to the trial or implantable device 100 size chosen, after the height (or width, depending on reference point) of the interspinous, interlaminar space 6 has been measured as described in the steps above. Once the interspinous space 6 has been evaluated, the user can hold the handles 22, 24 in this position while the knob 80 can be turned downward onto the shaft 76, as shown by the arrows in FIG. 4A, until the desired trial/implantable device size is reached on the size markings 84 of the main body 72, as shown in FIGS. 4B and 4C. At this point, the knob 80 fixes the handles 22, 24 relative to one another and the user can release his grip, as shown in FIG. 4B. The user can read the force applied by viewing the pointer 86. When the grip is released, the handles 22, 24 will spread open slightly. The user can twist or tighten the knob 80 onto the handle 24 once again until the original grip position is reached, and the correct size is indicated. At that point the corresponding applied force can also be checked. As shown in FIG. 5, the correctly sized trial 110 or implantable device 100 as measured can be chosen and the remaining implant steps to insert into the interspinous, interlaminar space can be completed.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. An instrument for evaluating an interspinous, interlaminar space between adjacent vertebrae, comprising:
a pair of handles connected at a pivoting hinge, each handle having a gripping portion at one end and extending into a leg extension at another, each of the leg extensions terminating at a tip having a bearing surface for engaging a bone surface, wherein the tip of each leg extension extends at an angle less than 180 degrees relative to the leg extensions,
a spring bias mechanism between the pair of handles, and
a combination distance and force measurement component in cooperation with the pair of handles, the component being configured to measure a distance of the interspinous, interlaminar space, and a force for maintaining said distance, wherein the combination distance and force measurement component includes a single main body coupled to at least one of the pair of handles, the main body including at one portion thereof a series of indicia representing units of distance and, at another portion thereof, a series of indicia representing units of force.

2. The instrument of claim 1, wherein each of the leg extensions extends at an angle relative to the handles in at least first and second intersecting planes.

3. The instrument of claim 2, wherein each of the leg extensions extends at a right angle relative to the handles in each of the first and second intersecting planes.

4. The instrument of claim 1, wherein the tips extend at a right angle relative to the leg extensions.

5. The instrument of claim 1, wherein the bearing surface includes a surface feature for enhanced bone contact.

6. The instrument of claim 1, wherein the spring bias mechanism comprises a pair of interconnected leaf springs.

7. The instrument of claim 1, wherein the combination distance and force measurement component is slidingly attached to one of the handles and fixedly attached to the other of the handles.

8. The instrument of claim 1, wherein the combination distance and force measurement component main body has a channel and a translatable shaft movable therein.

9. The instrument of claim 8, further including a knob for maintaining the handles in position relative to one another against the translatable shaft of the combination distance and force measurement component.

10. The instrument of claim 8, wherein the translatable shaft includes a band to indicate a measured unit of distance when viewed through a window of the main body near the indicia representing units of distance.

11. The instrument of claim 8, further including a pointer extending from one of the handles for resting against the main body near the series of indicia representing units of distance.

12. The instrument of claim 1, wherein movement of the gripping portion of the handles towards one another effects spreading apart of the tips.

13. The instrument of claim 1, wherein the units of distance are millimeters.

14. The instrument of claim 1, wherein the distance measured represents a height of the interspinous, interlaminar space between the adjacent vertebrae.

15. The instrument of claim 1, wherein the units of force are Newtons.

16. The instrument of claim 1, wherein the force measured represents an amount of tension between the adjacent vertebrae.

17. The instrument of claim 1, wherein the angle between each tip and each leg extension is in the range of about 60 to 120 degrees.

18. The instrument of claim 1, wherein the angle between each tip and each leg extension is in the range of about 75 to 105 degrees.

19. The instrument of claim 1, wherein the leg extensions and the tips are configured to bear a load.

20. An instrument for evaluating an interspinous, interlaminar space between adjacent vertebrae, comprising:
- a pair of handles connected at a pivoting hinge, each handle having a gripping portion at one end and extending into a leg extension at another, each of the leg extensions terminating at a tip having a bearing surface for engaging a bone surface,
- a spring bias mechanism between the pair of handles, and
- a combination distance and force measurement component in cooperation with the pair of handles, the component being configured to measure a distance of the interspinous, interlaminar space, and a force for maintaining said distance, the combination distance and force measurement component including a single main body coupled to at least one of the pair of handles, the main body including at one portion thereof a series of indicia representing units of distance and, at another portion thereof, a series of indicia representing units of force;
- wherein the leg extensions extend at an angle relative to the handles in at least first and second intersecting planes.

* * * * *